United States Patent
McKinnon et al.

(10) Patent No.: US 10,070,876 B2
(45) Date of Patent: Sep. 11, 2018

(54) PATIENT MATCHED INSTRUMENT

(71) Applicant: Smith & Nephew, Inc., Memphis, TN (US)

(72) Inventors: Brian W. McKinnon, Arlington, TN (US); Eric S. Kennedy, Memphis, TN (US); Michael J. Jackson, Southaven, MS (US); Randy C. Winebarger, Southaven, MS (US); Zachary C. Wilkinson, Germantown, TN (US)

(73) Assignee: Smith & Nephew, Inc., Memphis, TN (US)

( * ) Notice: Subject to any disclaimer, the term of this patent is extended or adjusted under 35 U.S.C. 154(b) by 616 days.

(21) Appl. No.: 14/414,725

(22) PCT Filed: Jul. 15, 2013

(86) PCT No.: PCT/US2013/050498
§ 371 (c)(1),
(2) Date: Jan. 14, 2015

(87) PCT Pub. No.: WO2014/014824
PCT Pub. Date: Jan. 23, 2014

(65) Prior Publication Data
US 2015/0201952 A1 Jul. 23, 2015

Related U.S. Application Data

(60) Provisional application No. 61/671,758, filed on Jul. 15, 2012, provisional application No. 61/681,440, (Continued)

(51) Int. Cl.
*A61B 17/15* (2006.01)
*A61B 17/17* (2006.01)
(Continued)

(52) U.S. Cl.
CPC ........ *A61B 17/1764* (2013.01); *A61B 17/155* (2013.01); *A61B 2017/568* (2013.01); *A61B 2034/108* (2016.02)

(58) Field of Classification Search
CPC ..................................................... A61B 17/155
See application file for complete search history.

(56) References Cited

U.S. PATENT DOCUMENTS

| 9,138,239 B2 * | 9/2015 | Aram | A61B 17/157 |
| 9,314,251 B2 * | 4/2016 | Aram | A61B 17/157 |

(Continued)

FOREIGN PATENT DOCUMENTS

| WO | 2009111512 A2 | 9/2009 |
| WO | 2011056995 A2 | 5/2011 |

(Continued)

OTHER PUBLICATIONS

Australian Examination Report No. 1; Australian Patent Office; Australian Patent Application No. 2013290427; dated Feb. 27, 2017; 3 pages.

(Continued)

*Primary Examiner* — Nicholas Woodall
(74) *Attorney, Agent, or Firm* — Pepper Hamilton LLP

(57) ABSTRACT

A patient matched instrument for a patient's femur is disclosed. The instrument includes a body having a cutting slot and a patient matched surface that mates with the patient's trochlear groove, a first leg portion extending from the body, a second leg portion extending from the body; and each leg portion has a contacting pad for tangential contact with the patient's femoral medial and lateral condyles.

26 Claims, 19 Drawing Sheets

Related U.S. Application Data filed on Aug. 9, 2012, provisional application No. 61/715,562, filed on Oct. 18, 2012.

(51) Int. Cl.
  *A61B 17/56* (2006.01)
  *A61B 34/10* (2016.01)

(56) References Cited

U.S. PATENT DOCUMENTS

| | | |
|---|---|---|
| 2009/0087276 A1 | 4/2009 | Rose |
| 2011/0092977 A1 | 4/2011 | Salehi et al. |
| 2012/0116562 A1 | 5/2012 | Agnihotri et al. |
| 2013/0317510 A1* | 11/2013 | Couture ............... A61B 17/154 606/88 |

FOREIGN PATENT DOCUMENTS

| | | |
|---|---|---|
| WO | 2012027402 A2 | 3/2012 |
| WO | 2012051542 A2 | 4/2012 |

OTHER PUBLICATIONS

Extended European Search Report; European Patent Office; European Application No. 13819526.8; dated Feb. 9, 2016; 8 pages.
European Examination Report; European Patent Office; European Application No. 13819526.8; dated Dec. 8, 2017; 4 pages.

\* cited by examiner

Fig. 22
Fig. 22a
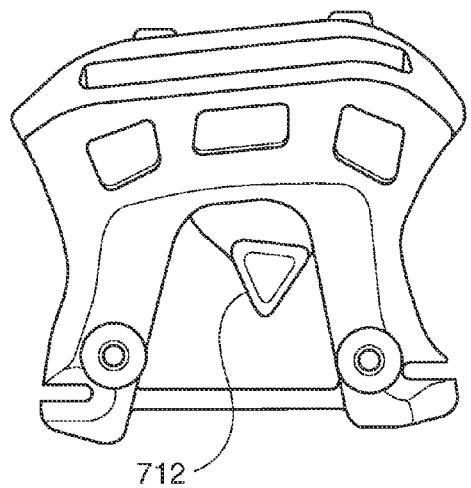
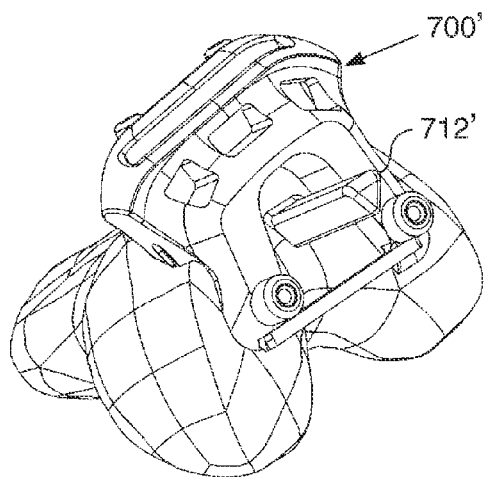
Fig. 22b
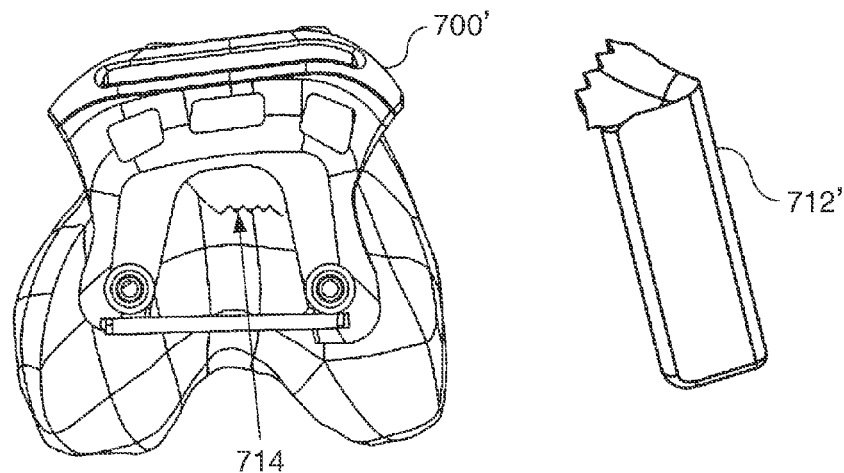

Fig. 23
Fig. 24
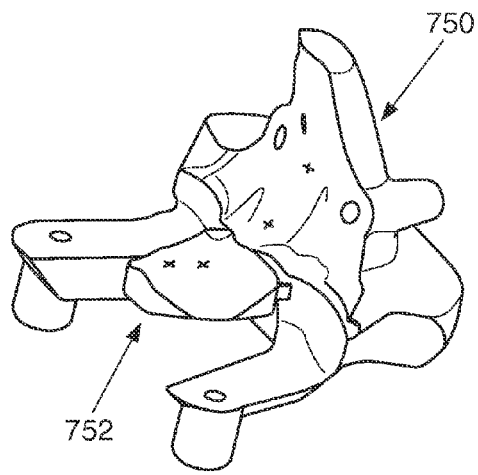
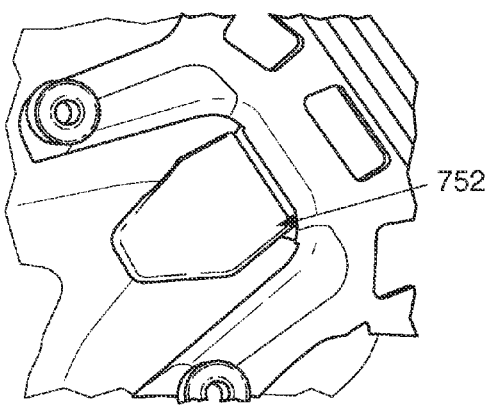
Fig. 25
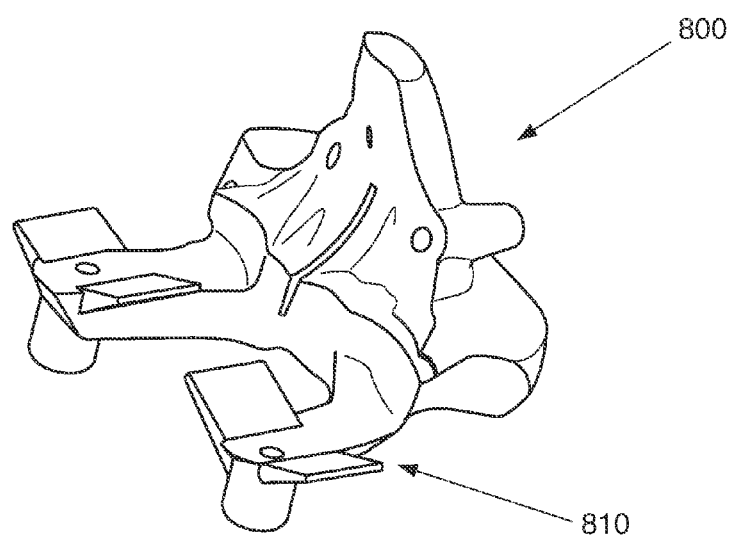

PATIENT MATCHED INSTRUMENT

CROSS-REFERENCE TO RELATED APPLICATIONS

This application is a United States National Phase filing of International Application No. PCT/US2013/050498, filed Jul. 15, 2013 which claims the benefit of U.S. Provisional Application No. 61/671,758, filed 15 Jul. 2012, of U.S. Provisional Application No. 61/681,440, filed 9 Aug. 2012, and of U.S. Provisional Application No. 61/715,562, filed 18 Oct. 2012. The disclosure of each prior application is incorporated by reference in its entirety.

BACKGROUND OF THE INVENTION

The present invention relates generally to surgical instruments and methods for the treatment of bones or joints, in some instances surgical instruments that are matched to a particular patient's anatomy, are described herein. Also described are methods of designing and using such surgical instruments.

Conventional patient-matched instruments are provided with large surfaces that are configured to conform to a patient's unique anatomy. Successful surgical outcomes depend on the ability of patient-matched instruments to provide a reproducible, "confident" 3D-fit between the patient-matched instrument and the anatomy that they are designed to rest against. If there is any doubt by an end user that a patient-matched instrument fits well upon repeated engagement with a patient's unique anatomy, or if the instrument appears to fit well with the patient's anatomy in multiple spatial orientations with respect to the anatomy, the instrument is typically discarded, and the surgery is carried out with the use of conventional, non-patient specific instruments.

To date, at least some patient-matched surgical instruments for use in total knee arthroplasty have employed anatomy-contacting surfaces that are substantially "negatives" of distal femoral and proximal tibial articular joint surfaces. The anatomy-contacting surfaces are generally large surface areas that conform in a continuous manner to substantial areas of a patient's anatomy. In some instances, the custom surgical instruments are provided by obtaining 3D image data of the patient's anatomy (e.g., via an MRI scan), segmenting the 3D image data to clearly delineate surfaces of the bony and/or cartilegeneous anatomy from surrounding tissues, converting the segmented data to a computer model via CAD or other software, performing one or more optional secondary processes (e.g., smoothing functions), using a computer model to customize one or more surfaces of an instrument to the patient's anatomy, and manufacturing the custom instrument such that it is adapted to conform to the patient's anatomy in a single spatial orientation.

In at least some current practices, substantially all portions of the joint anatomy shown in each 3D image data slice are segmented and conventional patient-matched instruments are provided with anatomy-contacting portions that contact substantially continuous areas of the patient's anatomy. Such anatomy-contacting portions have large continuous surface areas of contact with the patient's bone and cartilage, and therefore, it is critical that the engineers or automated programs creating the patient-matched instruments maintain a high level of accuracy and precision throughout each step of the entire segmentation process. Even if only one or two points on anatomy-contacting surfaces of a patient-matched instrument are inaccurate, misaligned, or otherwise misrepresent the true unique anatomy of the patient, the patient-matched instrument may not fit well, sit proud, teeter, wobble, or may not fit at all. In such instances, an end user is less likely to use the instrument. In many cases, poor patient-matched instrument fit may be attributed to even a few minor errors in the segmentation process.

SUMMARY OF THE INVENTION

The various embodiments of the present invention described below and shown in the Figures provide a patient matched instrument that is designed to provide improved repeatability and reproducibility over the prior art. The patient matched instrument includes a patient matched surfaces that mates with a patient's trochlear groove and two contacting pads for tangent contact with the patient's femoral condyles. The patient matched instrument incorporates design features that encourage consistent placement and accurate placement.

Further areas of applicability of the invention will become apparent from the detailed description provided hereinafter. It should be understood that the detailed description and specific examples, while indicating the particular embodiment of the invention, are intended for purposes of illustration only and are not intended to limit the scope of the invention.

BRIEF DESCRIPTION OF THE DRAWINGS

The accompanying drawings which is this case is a group of sketches prepared by the inventor and, which are incorporated in and form a part of the specification, illustrate the embodiments of the invention and together with the written description serve to explain the principles, characteristics, and features of the invention. In the drawings:

FIGS. 20-24 illustrate a distal trochlea notch grip.

FIG. 25 illustrates an embodiment of the patient matched instrument having tangent contact paddles.

DETAILED DESCRIPTION OF THE EMBODIMENTS

The following description of the depicted embodiment(s) is merely exemplary in nature and is in no way intended to limit the invention, its application, or uses.

Figure 1:
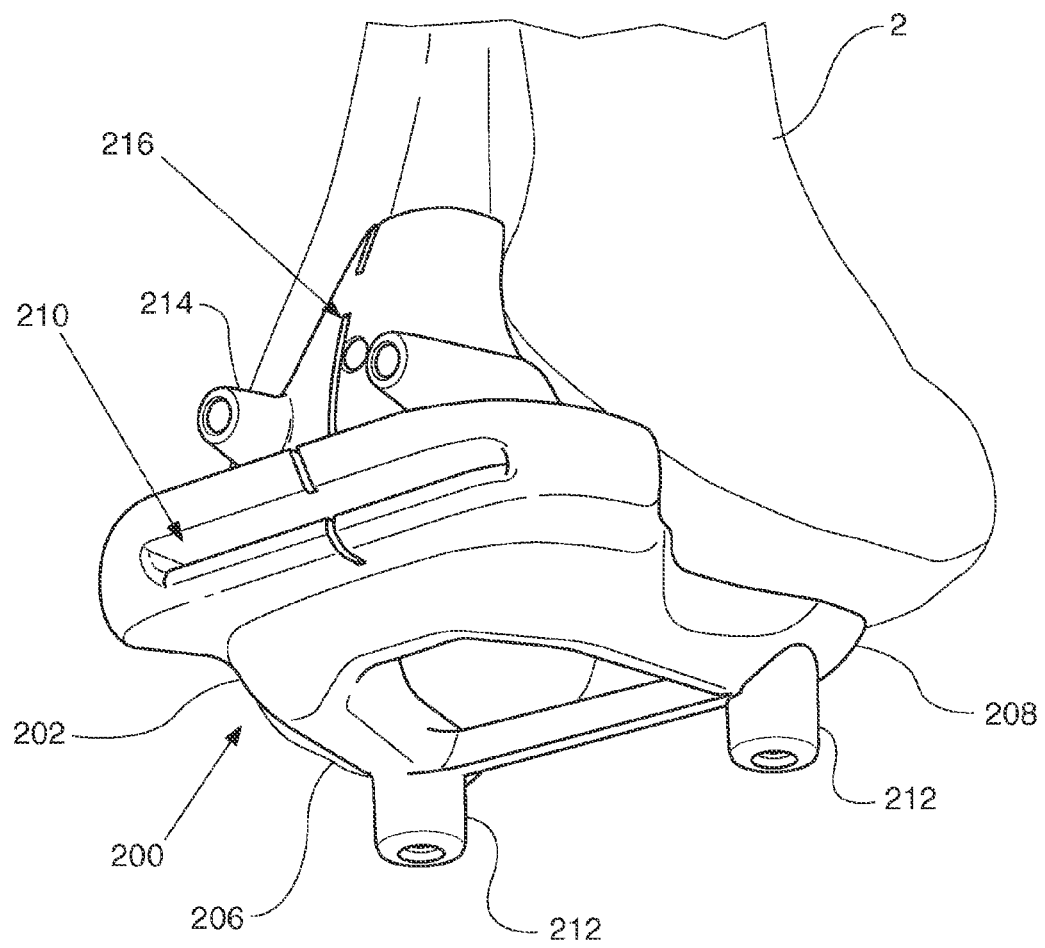
FIG. 1 shows a side perspective view of a patient matched instrument mounted on a left femur.

Embodiments of the present invention provide a patient matched instrument that is designed to provide improved repeatability and reproducibility over the prior art. FIG. 1 illustrates a patient matched instrument 200 placed on a femur 2. The patient matched instrument 200 is used to make a distal cut in knee arthroplasty. The patient matched instrument 200 includes a body 202. A first leg portion 206 and a second leg portion 208 extend from the body 202. The body includes a cutting slot 210 and one or more pin bosses 212 are located on each leg portion 206,208. In some embodiments, the patient matched instrument 200 also includes pin mounts 214. In use, the femur 2 is exposed via surgical incision. The patient matched cutting block 200 is placed on the femur 2 and located in a home position. Pins (not shown) are inserted into the pin bosses 212. Pins may be inserted into the pin mounts 214. A saw blade 4 (FIG. 2B) is reciprocated in the cutting slot 210 to remove bone from a distal end of the femur 2.

In some embodiments, the patient matched instrument 200 may include a visual indicator 216. In the depicted embodiment, the visual indicator 216 is formed by a groove, however, the visual indicator 216 also may be formed by other shapes or by other methods, such as painting or printing. As an example, the visual indicator 216 may align with the anterior-posterior (AP) axis or Whiteside's line of the femur 2. As another example, the visual indicator 216 may indicate the mechanical or anatomic axis of the femur 2.

Figure 2A:
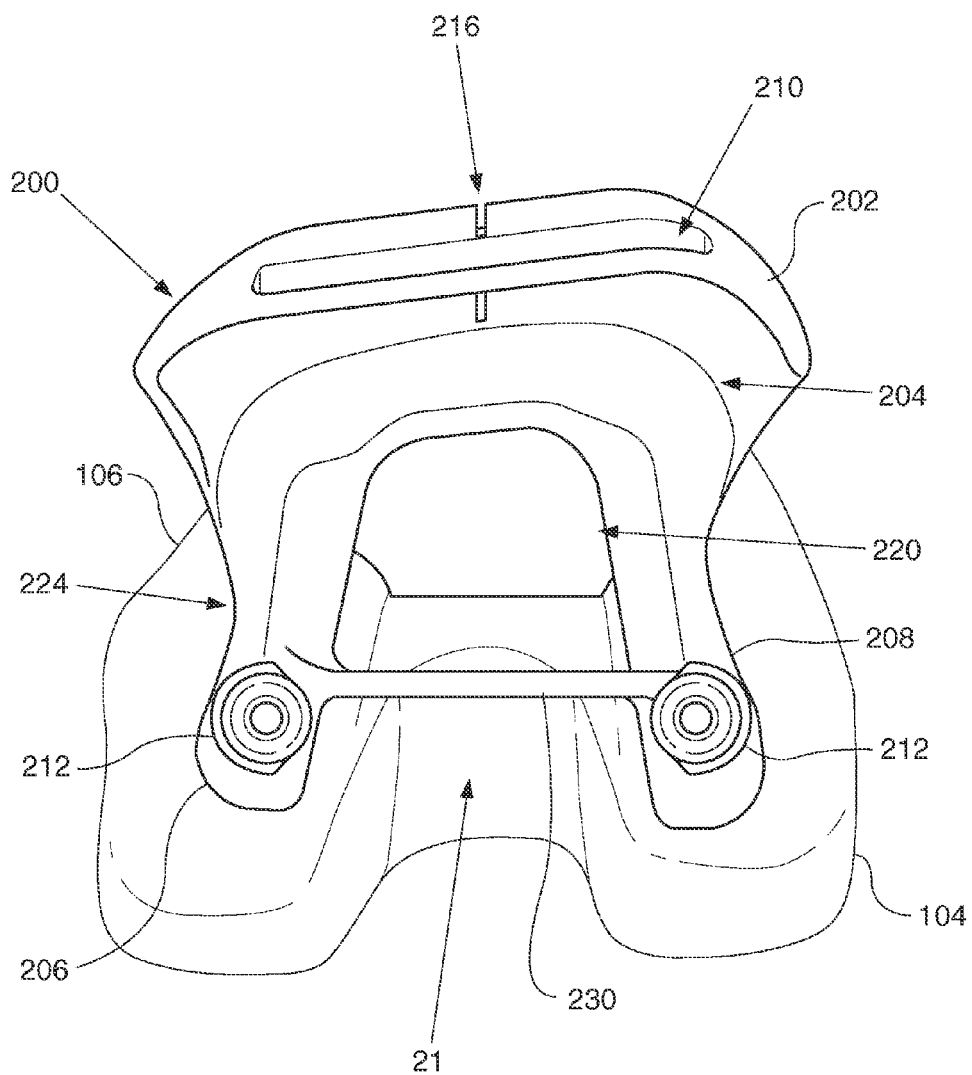
FIGS. 2A and 2B show an inferior-superior view of the patient matched instrument of FIG. 1.
Figure 2B:
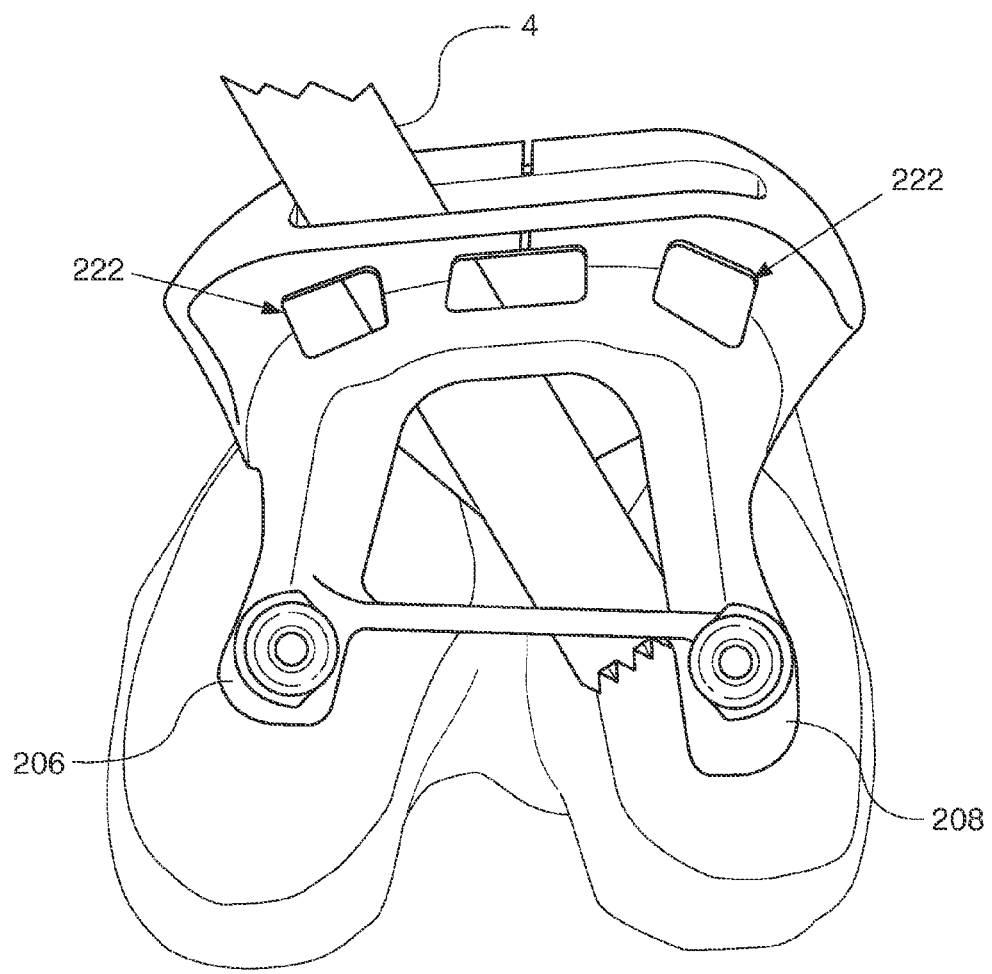

FIGS. 2A and 2B illustrate the patient matched instrument 200 mounted on the femur 2. The femur 2 has a medial condyle 106, a lateral condyle 104, and an intercondylar notch 21. Optionally, the patient matched instrument 200 may include a window 220. The window 220 allows an operator to see a saw blade 4 as it progresses in making the distal cut. As an example, the saw blade 4 may be seen in front of the intercondylar notch 21 between condylar portions 104,106 of the femur 2. In some embodiments, the patient matched instrument 200 includes one or more apertures 222. The aperture 222 may take any shape. For example, the aperture 222 may be square, rectangular, cylindrical, or trapezoidal. The patient matched instrument 200 includes a front surface 204

The patient matched instrument 200 includes the first leg portion 206 and the second leg portion 208. Each leg portion 206,208 includes one of the pin bosses 212. In some embodiments, each leg portion 204, 206 extends anteriorly in front of each condyle 104, 106. Each leg portion 206,208 may have a radiused face 224.

In some embodiments, the patient matched instrument 200 includes a guide 230. The guide 230 may be used to check for general alignment. For example, the guide 230 may align with the epicondylar axis, and a user may inspect the guide 230 compared to the epicondylar axis to check for general alignment of the patient matched instrument 200. The guide 230, if included, is also functional as it connects the first leg portion 206 to the second leg portion 208 for structural reinforcement. In the depicted embodiment, the guide 230 is substantially square and has a thickness of about 3 mm. Of course, other shapes, such as round, are possible, and also other dimensions are possible. For example, the guide 230 may have a cross-sectional diameter or width ranging from about 2 mm to about 15 mm, with a preferred range of about 3 mm to about 6 mm.

Figure 3:
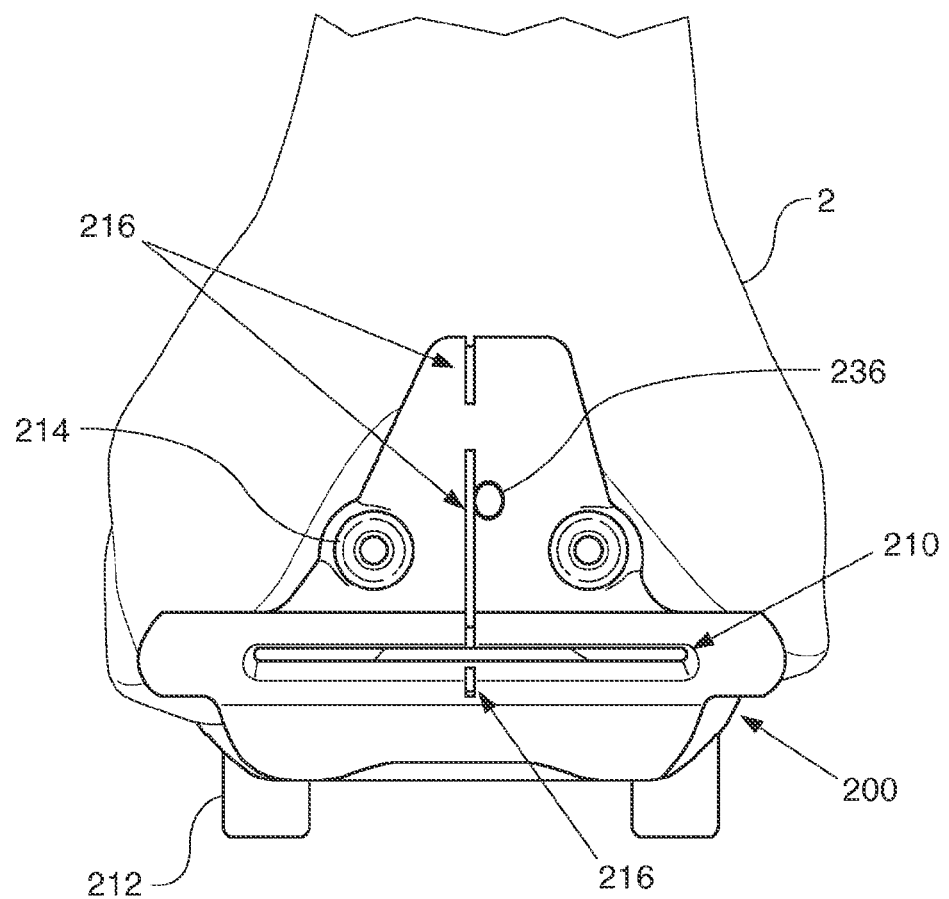
FIG. 3 shows an anterior-posterior view of the patient matched instrument of FIG. 1.

As shown in FIG. 3, the patient matched instrument 200 may include one or more additional fixation holes 236 to temporarily affix the patient matched instrument 200 to the femur 2. In some embodiments, the fixation hole 236 is angled relative to the cutting slot 210. For example, the fixation hole 236 may be angled from about 15 degrees to about 75 degrees. In the depicted embodiment, the fixation hole 236 is angled at about 45 degrees relative to the cutting slot 210. In some embodiments, the fixation hole 236 is aligned with the normal vector of the surface at the intersection of the hole axis and the anatomy surface. This may help reduce pinning error due to walking or skiving.

Figure 4:
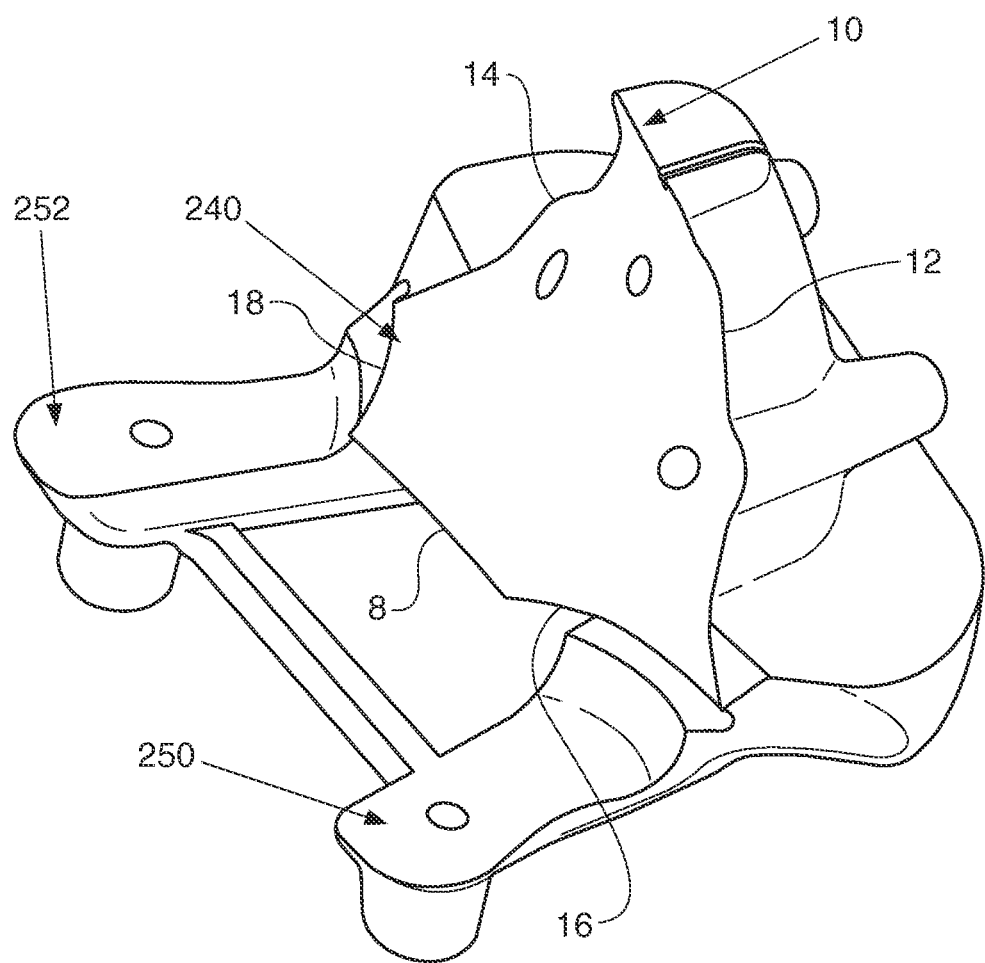
FIG. 4 shows a bottom perspective view of the patient matched instrument.

FIG. 4 illustrates the patient matched instrument 200 having a patient matched surface 240, a first contact pad 250, and a second contact pad 252. The patient matched surface 240 may be substantially defined by six boundary conditions 8, 10, 12, 14, 16, and 18 (outlined in FIG. 4 for visibility). In general, the patient matched surface 240 is custom-designed and manufactured to match the shape of and mate with a portion of a patient's trochlear groove. The first and second contact pads 250,252 are each generally planar and formed on each respective leg portion 206,208. The first and second contact pads 250,252 may be offset from one another in an anterior-posterior direction for varus/valgus constraint. The first and second contact pads are constructed and arranged to contact the utmost distal portions of the condyles 104,106. Due to the nature in which imaging data is obtained (i.e., 2 mm slices in a sagittal plane) and 3D bone anatomic models are produced, the combination of the trochlear groove contact in combination with the distal condyle contact provides a custom cutting block is the highly reproducible and repeatable. As more accurate data is available as to the utmost distal point of each condyle 104, 106, in some embodiments the contact pads 250,252 are the primary references and any other contact portion, such as in the trochlear groove, is secondary. This may be of significance for geometric tolerancing. Each of the first and second contact pads 250,252 may provide line contact, area contact, a plurality of contact points, or a single point of contact.

Figure 5:
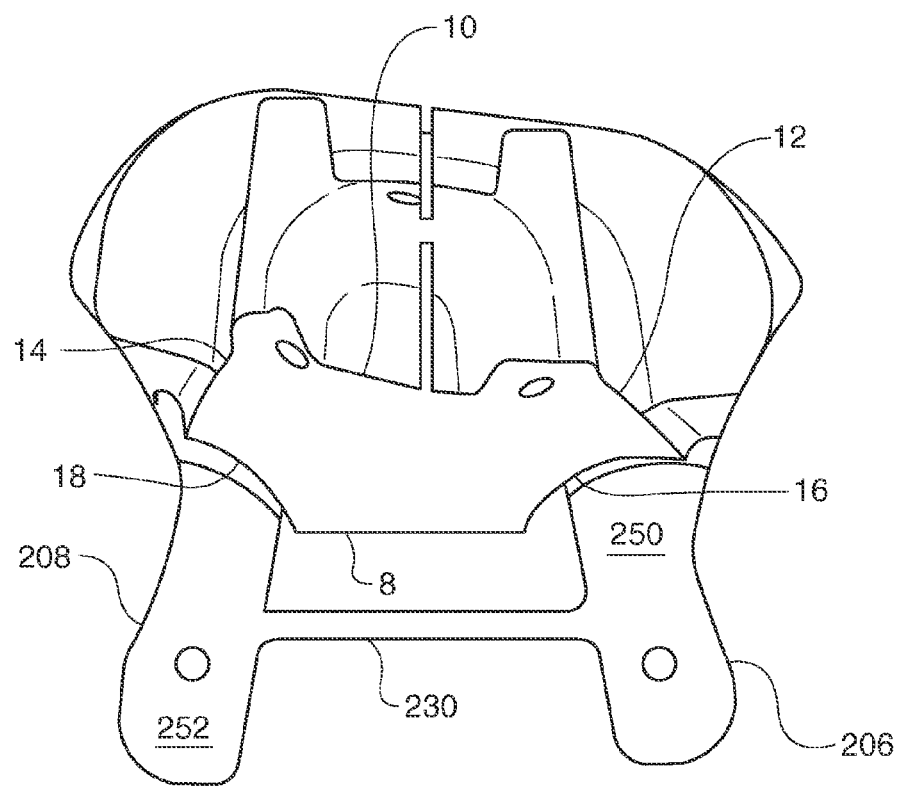
FIG. 5 shows a bottom view of the patient matched instrument.

As best seen in FIG. 5, the leg portions 206, 208 may be of different lengths. Also, the boundary 8 (described in greater detail below) has a straight edge appearance but need not have one.

Figure 6A:
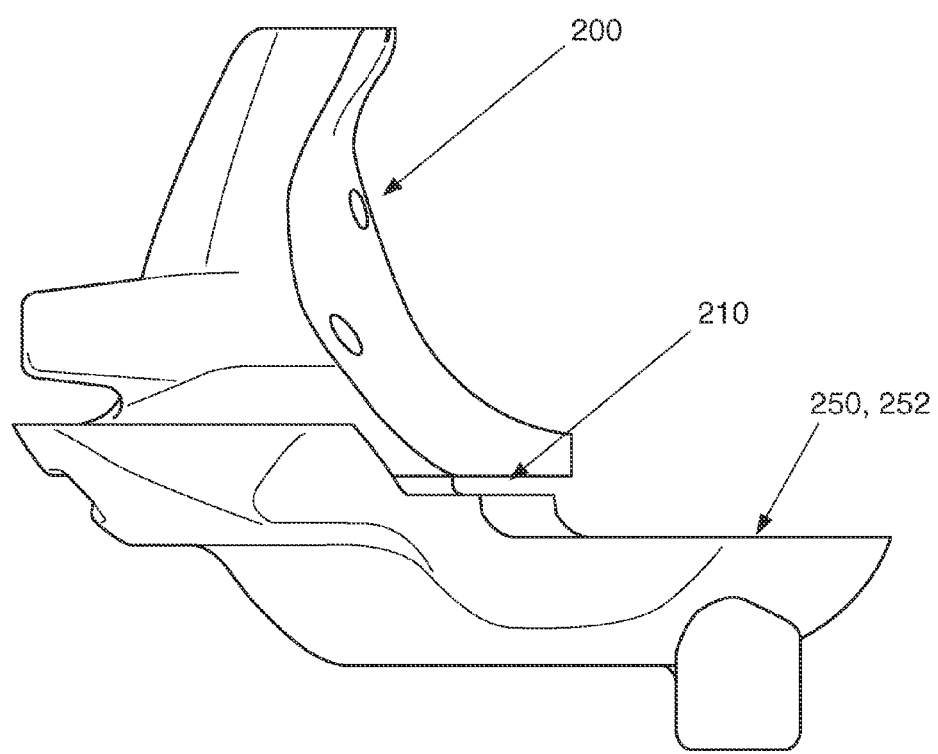
FIGS. 6A and 6B show a side view of two embodiments of the patient matched instrument.
Figure 6B:
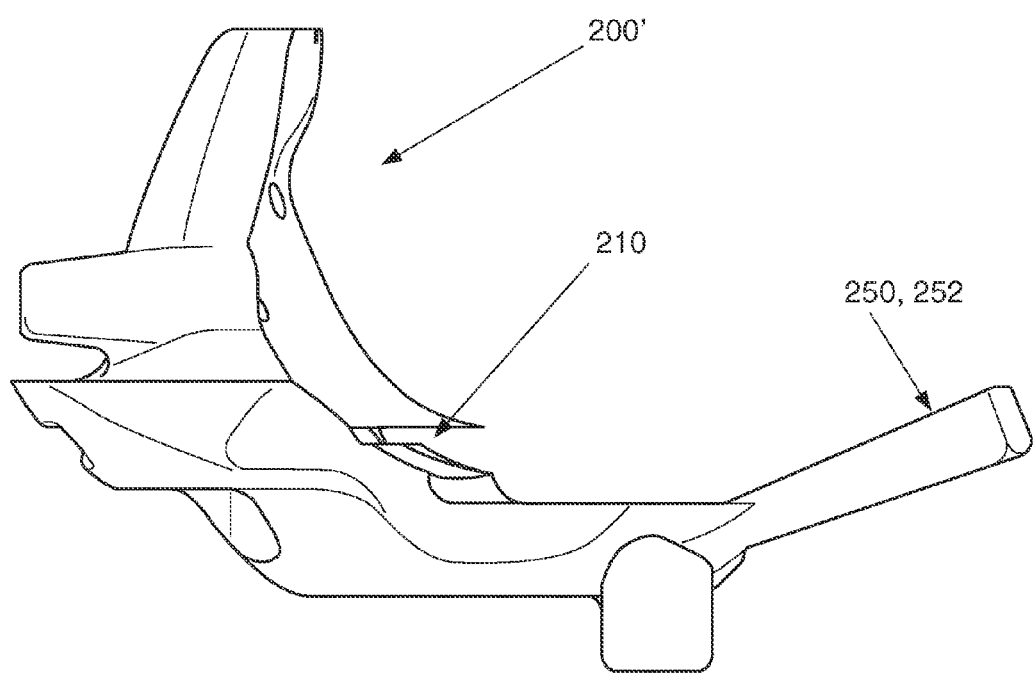

In the embodiment depicted in FIG. 6A, the first and second contact pads 250, 252 are generally parallel to the cutting slot 210 and/or substantially perpendicular to the mechanical axis. Those of ordinary skill in the art would understand that other arrangements are possible. For example, as shown in FIG. 6B, the first and second contact pads may be designed to contact other and/or additional portions of condyles 104, 106 at an angle relative to the cutting slot 210 and/or the mechanical axis.

Figure 7:
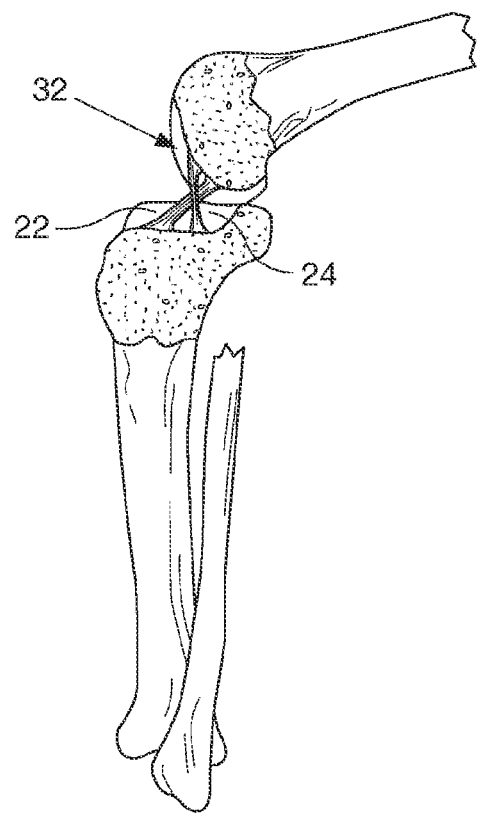
FIG. 7 is an exemplary illustration of a human right-side femur attached to a tibia by the anterior and the posterior cruciate ligaments.
Figure 8:
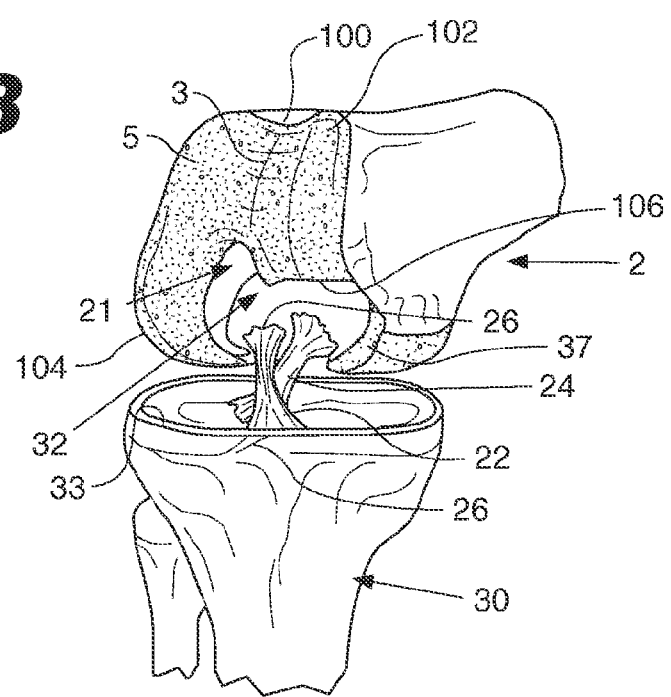
FIG. 8 is an expanded view of a human right-side knee joint in a bent position.

FIGS. 7 and 8 show exemplary views of a normal, intact knee joint. By way of background, a human knee joint includes two cruciate ligaments which are located in the center of the knee joint. As shown in FIG. 8, these two ligaments, referred to in the art as the anterior cruciate ligament (ACL) 22 and the posterior cruciate ligament (PCL) 24, are primary stabilizing ligaments of the knee. The ACL 22 attaches at its distal end 26 to the tibia 30, and passes obliquely upward into the inner and back part 32 of the lateral condyle 104 of the femur 2 for attachment at the proximal end. Attachment of the ACL 22 to the femur 2 stabilizes the knee joint along the anterior-posterior direction and prevents the femur 2 from sliding backwards on the tibia 30 (or the tibia from sliding forward on the femur).

In some embodiments, the first boundary condition 8 of the patient matched surface may be designed to not extend far back to impinge upon the cruciate attachments or the ligaments themselves. Therefore, the first boundary condition of a patient matched surface may be defined to be about 2 to about 13 mm from the point of attachment of the ACL 22 or the PCL 24 to the patient's femur 2. More specifically, as illustrated in FIG. 8, the first boundary condition 8 may be from about 3 mm to about 6 mm from the point of attachment 20 of the ACL 22 or PCL 24. In other words, there is about 2 mm to about 13 mm distance between the first boundary condition 8 and the attachment 20 of the ACL 22 or PCL 24. Alternatively, the first boundary condition of a patient matched surface 8 is within the intercondylar notch 21 but of a sufficient distance above where the ACL 22 or PCL 24 exits.

The second boundary condition 10 may be defined approximately at or near a superior edge 100 of an end of natural cartilage 102. In some embodiments, the patient matched surface 240 may extend slightly over the superior edge 100 to "hook" upon it. In other words, the second boundary condition 10 may have a lip to engage the superior edge 100. The third boundary condition 12 may be approximately at a top ridge of the lateral condyle 104. The fourth boundary condition 14 may be approximately at a top ridge of the medial condyle 106. The fifth and sixth boundary condition 16, 18 are angled upward and away from the condyles 104, 106 to provide clearance. The four boundary conditions 8, 10, 12, 14 as described above, may substantially define the perimeter or outer edges of the patient matched surface 240. However, the patient matched surface 240 need not be defined by any one of the four boundary conditions. Alternatively, the patient matched surface may be defined by any one of or any combination of the four boundary conditions. Of course, the perimeter or outer edges of individual patient matched surfaces may differ depending on the unique anatomic characteristics of an individual patient's femur.

Alternatively, a portion of the perimeter of the patient matched surface 240 may be defined by intersecting the cutting plane with a trochlear groove of the anatomic model. The resulting edge provides a general definition of the boundary condition edge 8. In other words, the patient matched surface 240 may be defined by intersecting boundaries of the anatomic model and the cutting plane. For example, the patient matched surface 240 is defined in a CAD model of the patient's anatomy by creating the distal cutting plane of the femur and defining the edge between cutting plane and the trochlear groove of the anatomic model.

Figure 9:
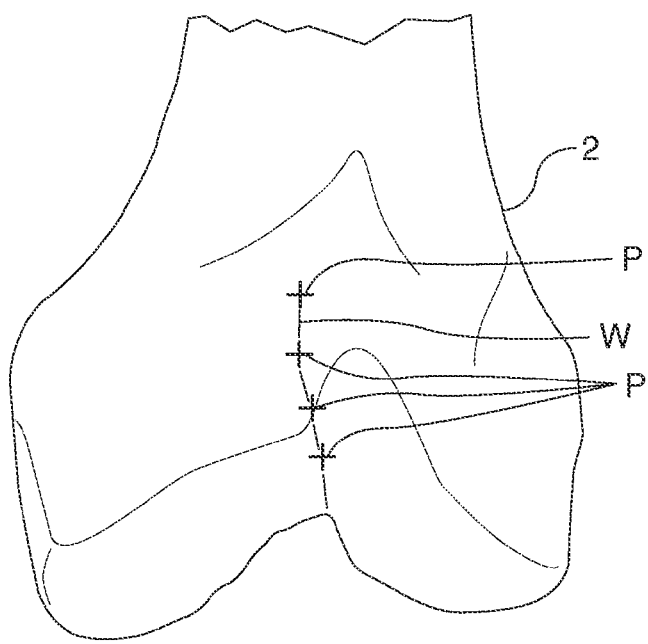
FIG. 9 illustrates the anterior trochlear sulcus which may be used to determine the AP axis.

As best seen in FIG. 9, a user may use points P on the femur 2 to generate a line W. Line W is indicative of the AP axis, a feature commonly used as a reference in knee surgery. As an example, a user may use a bovie to generate the points P and the line W.

Figure 10:
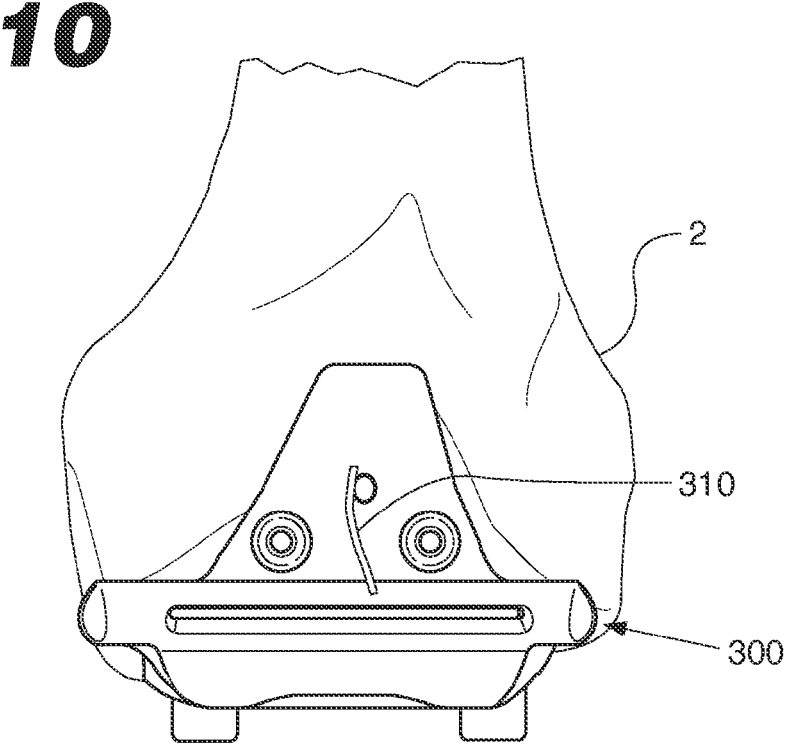
FIG. 10 illustrates an embodiment of the patient instrument with a window to view the AP axis.

FIG. 10 illustrates a patient matched instrument 300. The patient matched instrument has a passage 310. The passage 310 is customized for each individual patient. For example, an engineer or automated software landmarks low points of an anterior sulcus by creating points on a bone model created from imaging data in a modeling or imaging software. In one particular embodiment from about 4 to about 10 points are created on the bone model. The created points are connected with a line in the modeling or imaging software. This line forms the midline of the positive or negative AP line feature on the patient matched instrument. When the patient matched instrument is placed on the bone, the user can view the AP axis through the passage 310 for visual confirmation as to correct placement. Alternatively, the user can use the passage to trace the AP axis for use as a guide when the patient matched instrument is placed on the bone.

Figure 11A:
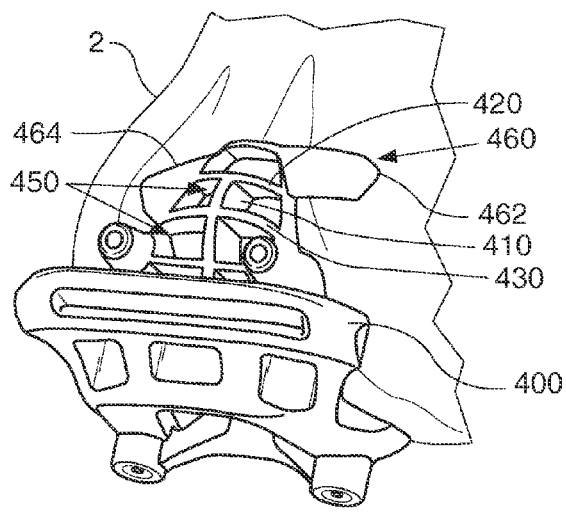
FIGS. 11a and 11b illustrate an embodiment with a grid opening to view the AP axis.

FIG. 11*a* illustrates a patient matched instrument 400. The patient matched instrument has a first cross-member 410, a second cross-member 420, and a third cross-member 430. The patient matched instrument 400 could have additional or fewer cross-members. The cross-members 410, 420, 430 form openings 450. The user can view the AP axis along the first cross-member 410 for visual confirmation as to correct placement. Additionally, a user can use openings 450 to visualize and confirm that cross-members 420,430 contact bone.

Figure 11B:
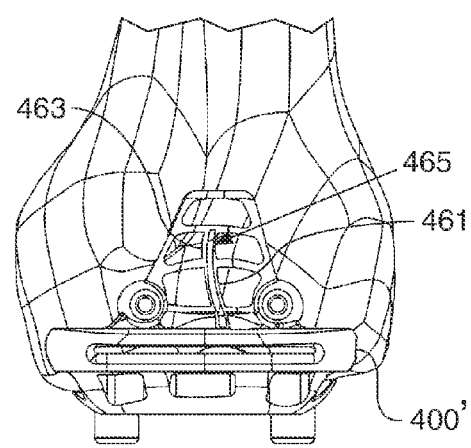

FIG. 11*b* illustrates a variation of the embodiment shown in FIG. 11*a*. In the depicted embodiment, the patient matched instrument 400' has a first cross member formed by a lateral member 461 and a medial member 463. The lateral and medial members 461, 461 are spaced apart to form a space 465. The user can view the AP axis through the space 465 for visual confirmation as to correct placement. Alternatively, the user can use the space 465 to trace the AP axis for use as a guide.

In some embodiments, the patient matched instrument 400 may include an anterior ridge extension 460. The anterior ridge extension 460 includes a first ear 462 and a second ear 464. In some embodiments, the anterior ridge extension 460 may include only the first ear 462 or the second ear 464. The anterior ridge extension 460 creates additional contact along both medial and lateral portions of the femoral anterior ridge.

Figure 12:
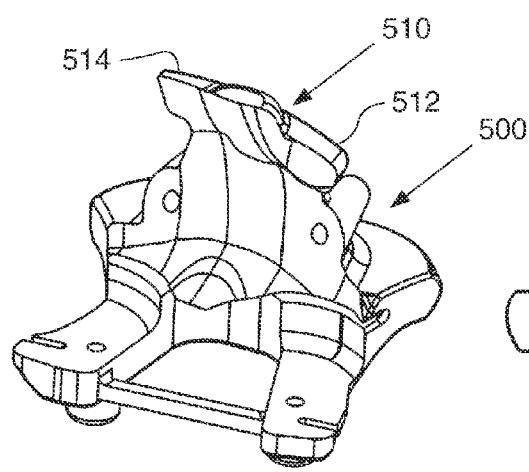
FIGS. 12-13 illustrate an embodiment having an anterior ridge extension.
Figure 13:
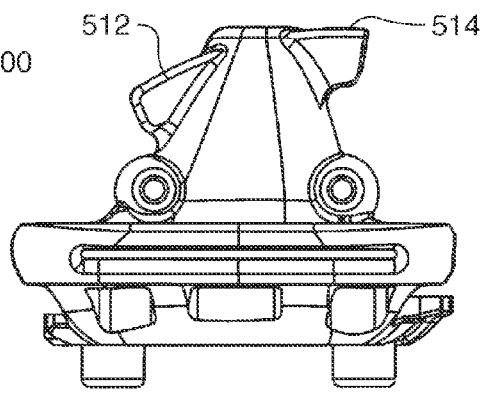

Alternative embodiments of the anterior ridge extension are shown in FIGS. 12 and 13. In the depicted embodiment, the patient matched instrument 500 includes an anterior ridge extension 510. The anterior ridge extension 510 includes a first ear 514 and a second ear 512. In some embodiments, the anterior ridge extension 510 may include only the first ear 514 or the second ear 512. The anterior ridge extension 510 creates additional contact along both medial and lateral portions of the femoral anterior ridge.

FIGS. 14-19 an embodiment having surface contact confirmation slots that help determine proper placement of a patient matched instrument as a visual check to ensure correct placement. In the depicted embodiment, the patient matched instrument 600 has a medial surface contact confirmation slot 610 and a lateral surface contact confirmation slot 612. The slots 610, 612 cut out of the distal paddles of the patient matched instrument denote a point that the distal femur makes contact with a tangent surface of the patient matched instrument. A user, such as surgeon, may place the patient matched instrument on the femur, view the patient matched instrument laterally and medially to verify that the slot outline lines up with the point where the patient matched instrument and bone meet. Although slots are shown in the depicted embodiment, those having ordinary skill in the art would understand that the confirmation feature could be negative (such as the slot) or positive. Further, instead of slots, other shapes, such as arrows or circles, may be used.

Figure 14:
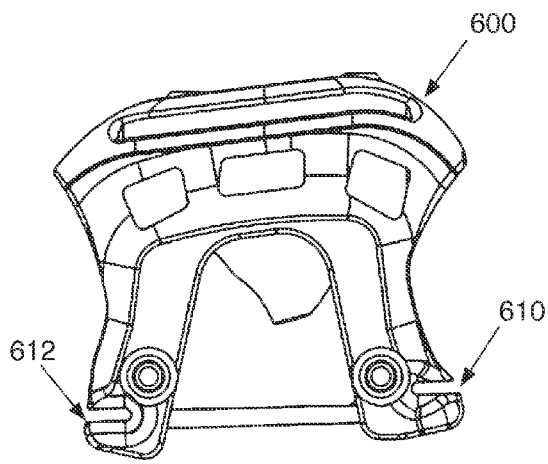
FIGS. 14-19 illustrate an embodiment having surface contact confirmation slots.
Figure 15:
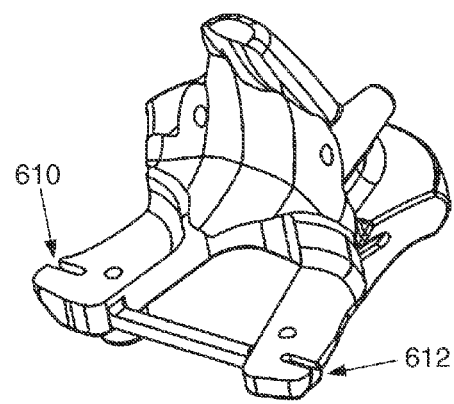
Figure 16:
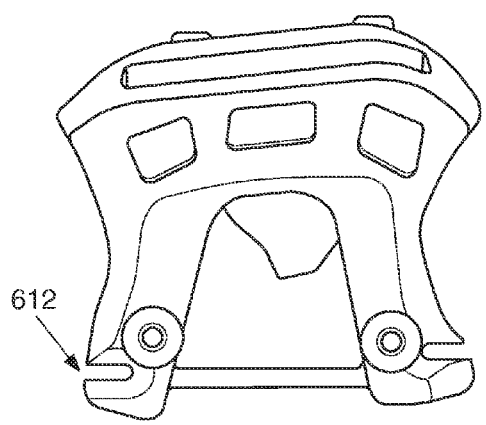
Figure 17:
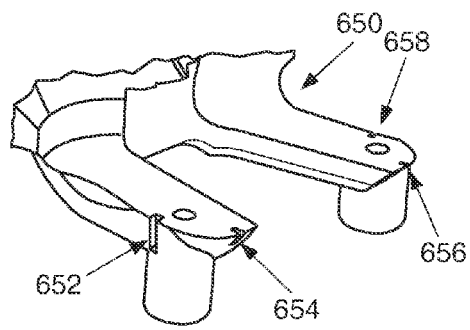
Figure 18:
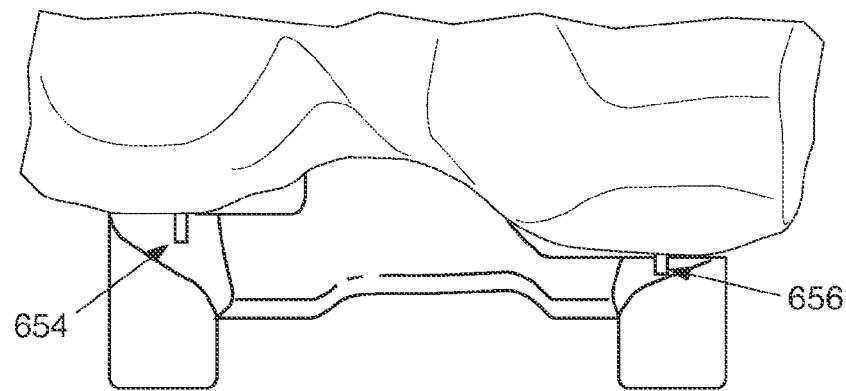
Figure 19:
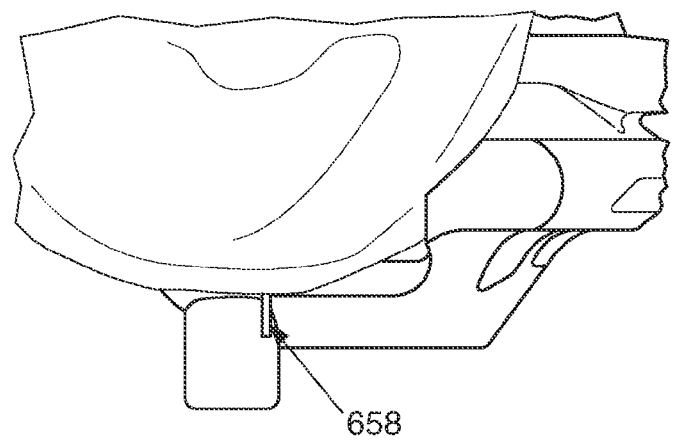

FIGS. 17-19 illustrate a variation of the embodiment shown in FIGS. 14-16. In the depicted embodiment, the patient matched instrument 650 includes not only medial and lateral slots 652, 658, but also distal slots 654, 656. In some embodiments, all or some of the slots 652, 654, 656, 658 may include color to increase visibility. For example, some of the slots may be colored red or yellow. The slots 652, 654, 656, 658 are sized and shaped to line up with only one point. A user view the femur posteriorly and sagittally to confirm the slots where the patient matched instrument contacts bone.

FIGS. 20-24 illustrate a distal trochlea notch grip. The notch grip is a portion of the patient matched instrument that is extended to contact and conform to the distal trochlea. In a first embodiment, the patient matched instrument 700 includes a distal trochlea notch grip 712. In some embodiments, the patient matched instrument 700' has a frangible distal trochlea grip 712' that is constructed and arranged to break at an area 714. The part is frangible after fixation to eliminate interference with resection. In some embodiments, the distal trochlea notch grip is combined with the anterior ridge extension to aid in capturing the patient matched instrument in two relatively opposed locations.

Figure 20:
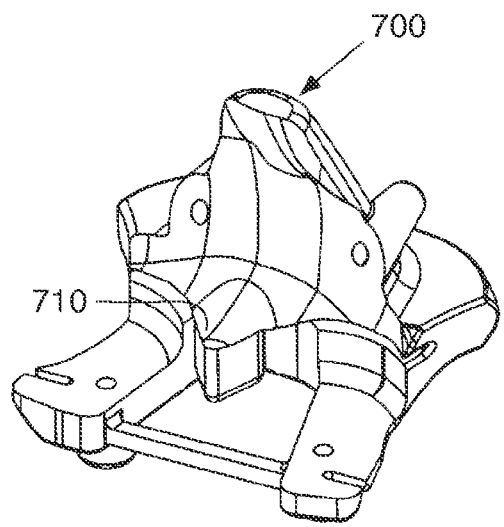
Figure 21:
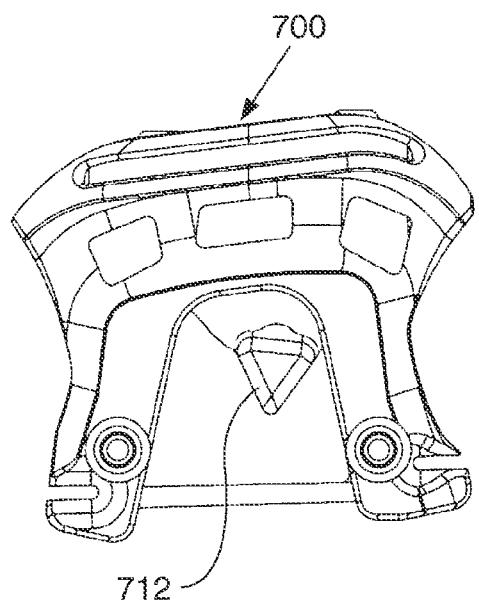
Figure 22C:
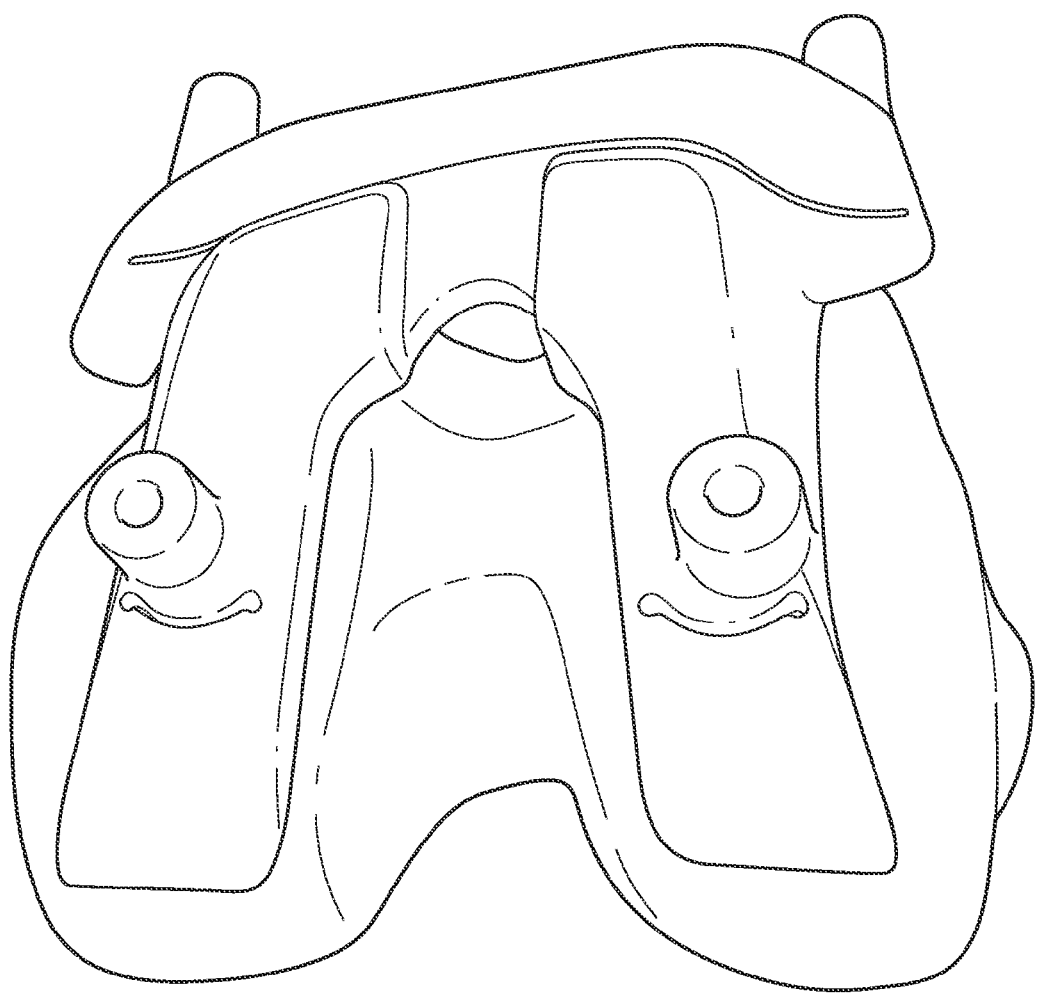

The second embodiment, depicted in FIGS. 23-24, illustrates a patient matched instrument 750 with a somewhat wider and larger distal trochlea notch grip 752 than the one shown in FIGS. 20-22. As with the first embodiment, the distal trochlea notch grip 752 may be frangible in some instances.

Other portions also may be removed in a similar manner to remove resection-obscuring features. For example, in the embodiment depicted in FIG. 22c apertures may be provided on or in each leg portion such that such components may be removed intraoperatively. The distal paddles may be important for initial placement stability and/or for guiding creation of distal pin hole datums, but the distal paddles may be unnecessary after the cutting block is fixated to the bone. The apertures allow the distal paddles to be removed after fixation if desired or if the paddles prevent or limit viewing a resection of bone.

FIG. 25 illustrates an embodiment of the patient matched instrument 800 having paddles 810. The paddles 810 provide angled, tangent contact with each femoral condyle to provide additional rotational stability.

Figure 26:
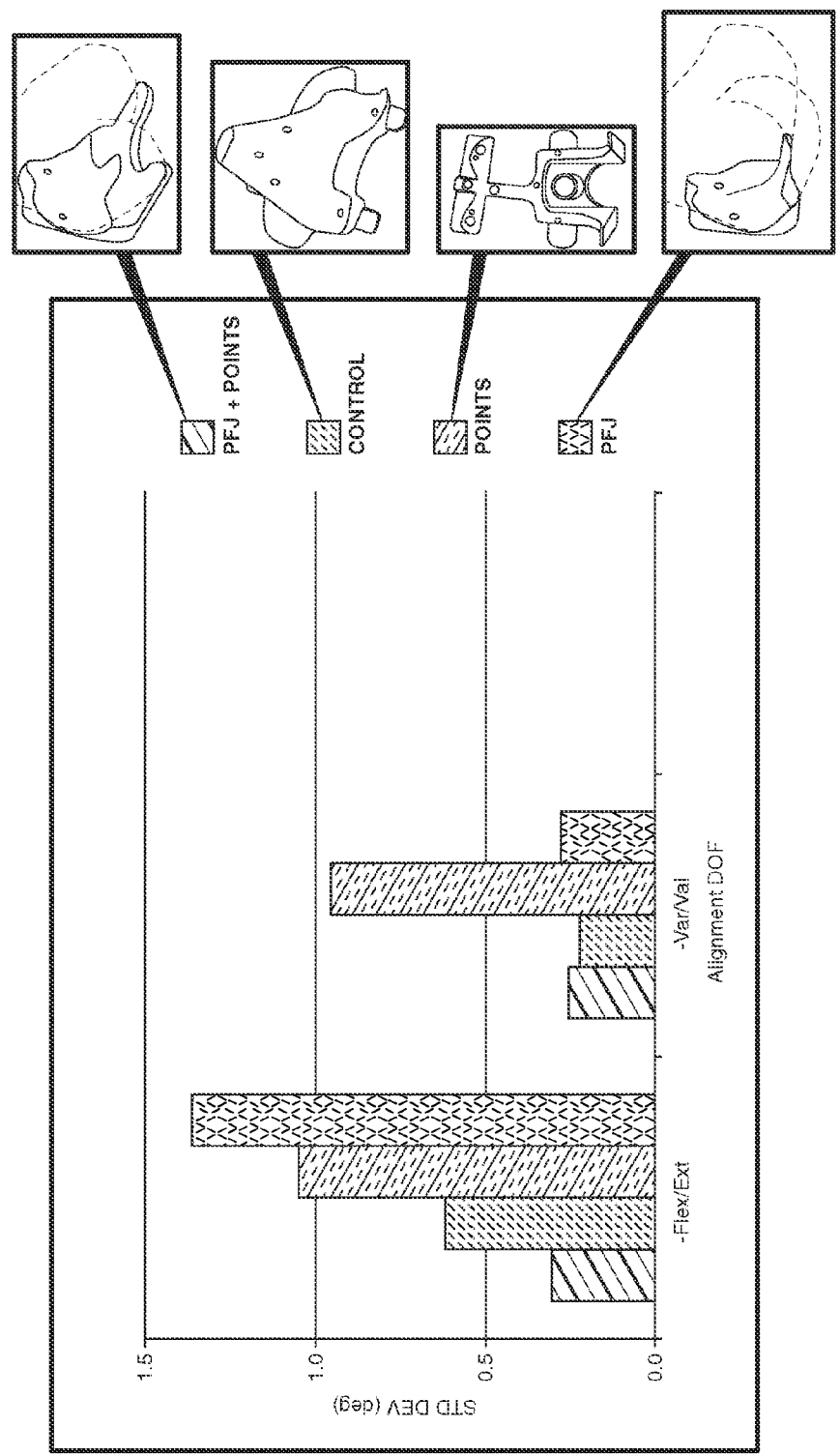
FIGS. 26 and 27 graphically illustrate the consistency and accuracy provided by the present invention.
Figure 27:
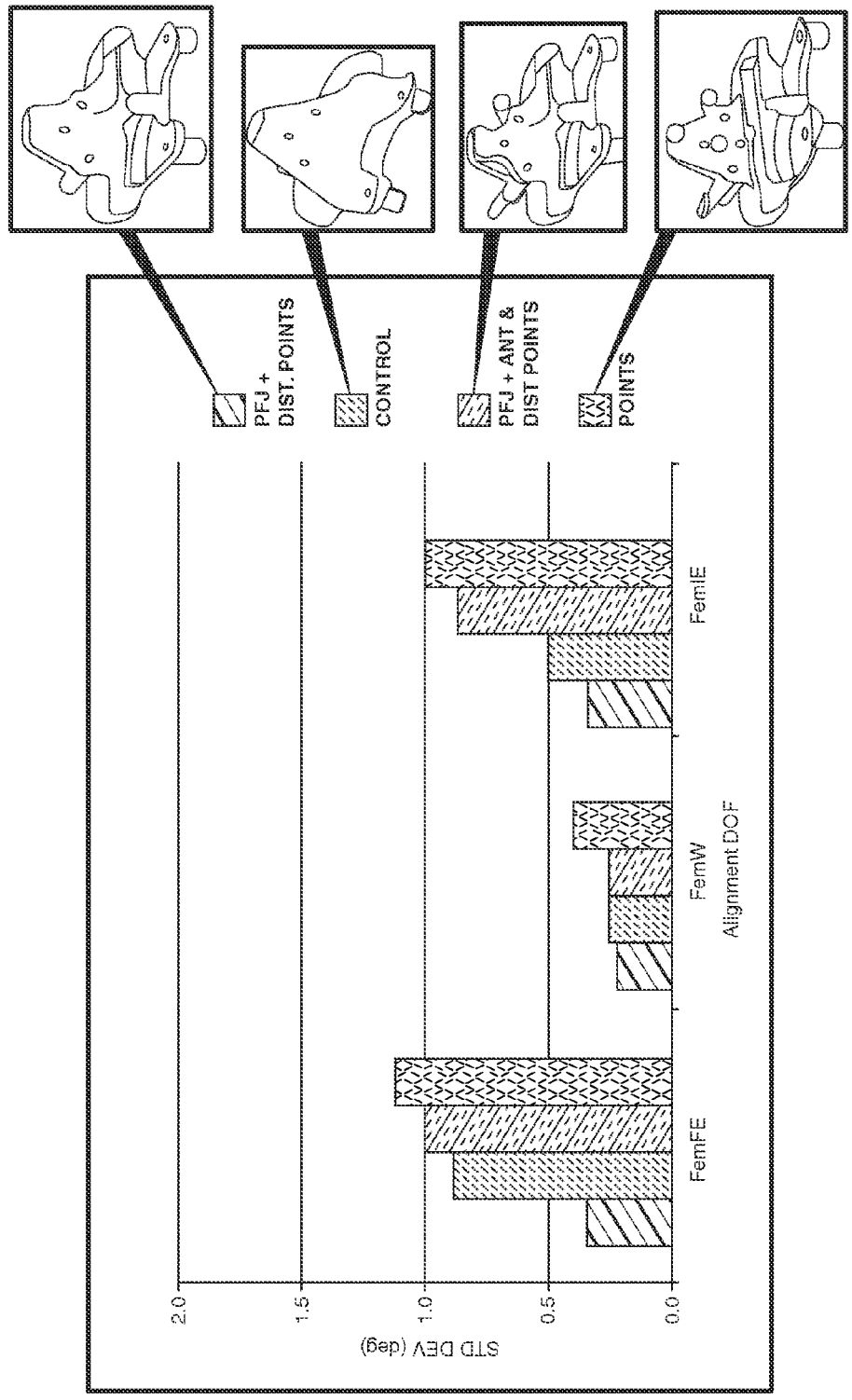

FIGS. 26 and 27 graphically illustrate results of lab testing of the disclosed embodiments. The protocol consisted of three operators performing three to five placement of each block design on a cadaver bone. Three degrees of freedom were measured with a computer assisted surgery (CAS) system for each individual placement. Specifically, these were: (1) varus/valgus rotation angle; (2) flexion/extension rotation angle; and (3) internal/external rotation angle. The standard deviation of all placements for a given block design was calculated for each degree of freedom. FIGS. 26 and 27 illustrate that the present invention (named "PFJ+Points" on the graphs) had the lowest standard deviation of all tested devices. Further, FIG. 27 illustrates that reducing the PFJ contact portion and replacing it with a somewhat truncated contact with several points (named "Points" on the graphs) was less than optimal but not necessarily unacceptable. There may be a threshold where the area/point contact trade off becomes "even" (as determined by the constraint provided), and as such it may be best described as a "point density" (points per unit area) rather than a specific number of points that is optimal. Also, that point density could vary over the surface. In some embodiments, full PFJ-area contact may be replaced by a range of point contact densities that are functionally equivalent or superior to full area contact. As an example, the range may be about 5 points/cm^2 to about 30 points/cm^2.

The term "substantially" as used herein may be applied to modify any quantitative representation which could permissibly vary without resulting in a change in the basic function to which it is related. For example, the contacting pads are disclosed as being substantially perpendicular to the mechanical axis and may permissibly have some variation from being truly perpendicular and still be within the scope of the invention if the function of the contacting pads are not materially altered.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. For example, while FIG. 1 illustrates pin bosses that receive pins other structure and/or methods may be used to temporarily affix the patient matched instrument to the femur. Thus, the breadth and scope of the present invention should not be limited by any of the above-described exemplary embodiments, but should be defined only in accordance with the following claims appended hereto and their equivalents.

What is claimed is:

1. A patient matched instrument for a patient's femur having a trochlear groove, a medial condyle, and a lateral condyle, the instrument comprising:
   a. a body having a cutting slot and a patient matched surface that mates with and contacts the patient's trochlear groove;
   b. a first leg portion extending from the body;
   c. a second leg portion extending from the body; and
   d. wherein each leg portion has a contacting pad for tangential contact with the patient's distal portion of femoral medial condyle and distal portion of femoral lateral condyle.

2. The instrument of claim 1, the body further comprising a visual indicator.

3. The instrument of claim 1, the body further comprising a window.

4. The instrument of claim 1, the body further comprising apertures.

5. The instrument of claim 1, wherein each leg portion further comprises at least one pin boss.

6. The instrument of claim 1, further comprising a guide.

7. The instrument of claim 1, wherein the patient matched surface of the body has six boundary conditions.

8. The instrument of claim 1, wherein the first leg portion has a different length from the second leg portion.

9. The instrument of claim 1, wherein the contacting pads are substantially perpendicular to a mechanical axis of the patient's femur.

10. The instrument of claim 1, wherein the contacting pads are parallel to the cutting slot.

11. The instrument of claim 1, wherein the contacting pads contact the femoral condyles at an angle relative to the cutting slot and/or the mechanical axis.

12. The instrument of claim 1, the body further comprising a passage.

13. The instrument of claim 1, wherein the body includes at least one cross-member.

14. The instrument of claim 1, wherein the body further comprises an anterior ridge extension.

15. The instrument of claim 1, further comprising at least one surface contact confirmation slot.

16. The instrument of claim 1, further comprising a distal trochlea grip.

17. The instrument of claim 1, wherein each leg portion includes at least one paddle.

18. The instrument of claim 1, wherein the body further comprises a frangible component.

19. The instrument of claim 18, wherein the frangible component is a leg portion.

20. The instrument of claim 1, wherein the body further comprises at least one fixation hole.

21. The instrument of claim 20, wherein the at least one fixation hole is aligned to a normal of a surface that the at least one fixation hole intersects.

22. The instrument of claim 7, wherein a first boundary condition of the six boundary conditions is positioned between 2 and 13 millimeters from a point of attachment of an anterior cruciate ligament or a posterior cruciate ligament to the patient's femur.

23. The instrument of claim 22, wherein a second boundary condition of the six boundary conditions is configured to engage a superior edge of an end of natural cartilage of the patient's femur.

24. The instrument of claim 23, wherein a third boundary condition of the six boundary conditions is configured to extend to a top ridge of the lateral condyle.

25. The instrument of claim 24, wherein a fourth boundary condition of the six boundary conditions is configured to extend to a top ridge of the medial condyle.

26. The instrument of claim 25, wherein a fifth boundary condition of the six boundary conditions is configured to extend away from the lateral condyle and a sixth boundary condition of the six boundary conditions is configured to extend away from the medial condyle.

* * * * *